United States Patent [19]

Murahashi et al.

[11] Patent Number: 5,466,838
[45] Date of Patent: Nov. 14, 1995

[54] PROCESS FOR PRODUCING EPOXIDE

[75] Inventors: Shun-Ichi Murahashi, Ikeda; Yoshiaki Oda, Toyonaka, both of Japan

[73] Assignee: Sumitomo Chemical Company, Limited, Osaka, Japan

[21] Appl. No.: 275,727

[22] Filed: Jul. 19, 1994

Related U.S. Application Data

[62] Division of Ser. No. 968,414, Oct. 29, 1992, Pat. No. 5,367,087.

[30] Foreign Application Priority Data

Oct. 30, 1991 [JP] Japan .................................. 3-284651
Mar. 11, 1992 [JP] Japan .................................. 4-052438
Mar. 11, 1992 [JP] Japan .................................. 4-052441

[51] Int. Cl.$^6$ ...................... C07D 301/06; C07D 303/04
[52] U.S. Cl. ........................ 549/533; 549/543; 549/545; 549/546
[58] Field of Search ............................... 549/533

[56] References Cited

U.S. PATENT DOCUMENTS

| | | | |
|---|---|---|---|
| 3,232,957 | 2/1966 | Sharp | 549/533 |
| 3,265,716 | 8/1966 | Dickey et al. | |
| 3,347,763 | 10/1967 | Coffey et al. | 549/533 |
| 3,379,737 | 4/1968 | Rustin et al. | 549/533 |
| 3,629,294 | 12/1971 | Sun | 549/533 |
| 4,483,998 | 11/1984 | Sanderson et al. | 549/533 |

FOREIGN PATENT DOCUMENTS

| | | | |
|---|---|---|---|
| 682335 | 6/1966 | Belgium . | |
| 1323787 | 3/1963 | France . | |
| 1367771 | 7/1963 | France . | |
| 1377981 | 9/1964 | France . | |
| 1376471 | 9/1964 | France . | |
| 1400305 | 4/1965 | France . | |
| 1594466 | 7/1970 | France . | |
| 2073743 | 11/1971 | France . | |
| 1161881 | 1/1964 | Germany | 549/533 |
| 1280234 | 10/1968 | Germany | 549/533 |
| 1568407 | 4/1970 | Germany . | |
| 1937387 | 2/1971 | Germany . | |
| 42625 | 12/1973 | Japan | 549/533 |
| 59-231077 | 12/1984 | Japan . | |
| 495079 | 3/1992 | Japan . | |
| 1051086 | 10/1983 | U.S.S.R. | 549/533 |
| 1143577 | 2/1969 | United Kingdom . | |
| 1240843 | 7/1971 | United Kingdom . | |
| 1308380 | 2/1973 | United Kingdom . | |
| 1329987 | 9/1973 | United Kingdom . | |

OTHER PUBLICATIONS

Daniel Swern et al, "Epoxidation of Oleic Acid, Methyl Oleate and Oleyl Alcohol with Perbenzoic Acid", Journal of American Chemical Society, vol. 66, pp. 1925–1927, Nov. 1994.

Synthesis, Communications, pp. 711–713, Oct. 1977, Iieinz Kropf et al.

Tsuneo Ikawa et al, "Liquid–Phase Oxidation of Cyclohexene in the Presence of Benzaldehyde", Canadian Journal Chemical Society, vol. 44, pp. 1817–1825, Jan. 1966.

Fujio Tsuchiya et al, "Liquid–phase Oxidation of 2–Butene in the Presence of Benzaldehyde", Canadian Journal of Chemical Society, vol. 47, pp. 3191–3197, Feb. 1969.

Uspekhi Khimii, "Reaction Mechanisms of the Direct Expoxidation of Alkenes in the Liquid Phase", Russian Chemical Reviews, vol. 44, pp. 807–821, Oct. 1972.

Tohru Yamada et al, "Direct Epoxidation of Olefins Catalyzed by Nickel(II) Complexes with Molecular Oxygen and Aldehydes", Bull. Chem. Soc. Jpn. vol. 64 pp. 2109–2117, Jul. 1991.

Toshihiro Takai et al, "Aerobic Epoxidation of Olefinic Compounds Catalyzed by Tris (1,3–diketonato)iron (III)", Bull. Chem. Soc. Jpn., vol. 64, pp. 2513–2518, Aug. 1991.

Jerzy Haber et al, "Reactivity–Structure Correlations in Oxidation with Metalloporphyrins", Journal of Molecular Catalysis, vol. 52, pp. 85–97, (1989).

Kenton R. Rodgers et al, "Iron Porphyrin Catalysed Oxidation of Propanal and Cyclohexene by Molecular Oxygen", Journal Chemical Society Communication, pp. 1323–1324, (1990).

Primary Examiner—Joseph E. Evans
Attorney, Agent, or Firm—Cushman Darby & Cushman

[57] ABSTRACT

A process for producing an epoxide represented by the formula (2) which comprises reacting an olefin represented by the formula (1) with oxygen in the presence of an aldehyde and in the presence or absence of a proton source by using no catalyst or using an iron-containing or copper-containing catalyst.

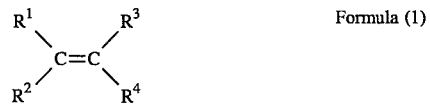

Formula (1)

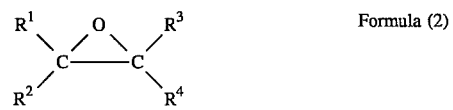

Formula (2)

12 Claims, No Drawings

PROCESS FOR PRODUCING EPOXIDE

This is a division of application No. 07/968,414, filed Oct. 29, 1992, now U.S. Pat. No. 5,367,087.

BACKGROUND OF THE INVENTION

1. Field of the Invention

The present invention relates to a process for producing an epoxide represented by the formula (2) shown later.

The epoxide mentioned above is important as an intermediate in producing a wide variety of products, including perfumes, pharmaceuticals, agricultural chemicals, liquid crystals and resins.

2. Description of the Related Art

It is well known to convert an olefin to the corresponding epoxide by using peracids such as peracetic acid, m-chloroperbenzoic acid, and the like (Some Modern Methods of Organic Synthesis, 3rd ed., P. 370–373). However, since peracids are highly sensitive to shock and are explosive, this method cannot be said to be an advantageous process from the industrial point of view.

To overcome such difficulty, processes have already been developed which comprise oxidizing an olefin with oxygen in the presence of an aldehyde by using a catalyst containing a soluble praseodymium compound (Japanese Patent Application KOKAI No. 59-231077) or a soluble nickel catalyst (Chem. Lett., 1991, 1). However, since these processes use a homogeneous catalyst, they require complicated operations in the separation of the epoxide, the intended product, from the catalyst and in the recovery of the catalyst, and further, when the catalyst is not recovered, the processes will produce a waste water with a high content of undesirable substances. Thus, they are not fully satisfactory as industrial processes.

The object of the present invention is to provide an advantageous process for producing epoxides by oxidizing olefins with oxygen in the presence of an aldehyde which uses no catalyst or uses a catalyst that in easily available and recoverable and that will bring little of undesirable substances into the waste water.

SUMMARY OF THE INVENTION

The present inventors have made extensive study to solve the above-mentioned problems, and resultantly attained the present invention.

Thus, according to the present invention, there is provided a process for producing an epoxide represented by the formula (2)

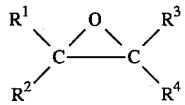

wherein $R^1$, $R^2$, $R^3$ and $R^4$ may be the same or different and each denotes a hydrogen atom, $(C_1-C_{20})$alkyl group; alkyl group substituted with a halogen, hydroxy, alkoxy, phenoxy, acyloxy, acyl, alkoxycarbonyl or phenoxycarbonyl; phenyl group, phenyl group substituted with a halogen, alkyl, alkoxy, phenoxy, acyloxy, acyl, alkoxycarbonyl or phenoxycarbonyl; phenylalkyl group, phenylalkyl group substituted with a halogen, alkyl, alkoxy, phenoxy, acyloxy, acyl, alkoxycarbonyl or phenoxycarbonyl; acyl group, alkoxycarbonyl group or phenoxycarbonyl group; provided that $R^1$ and $R^2$ or $R^1$ and $R^3$ may combine with each other to form a ring, or $R^1$, $R^2$ and $R^3$ may combine altogether to form a condensed ring, which comprises reacting an olefin represented by the formula (1)

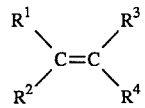

wherein $R^1$, $R^2$, $R^3$ and $R^4$ are the same as defined above, with oxygen in the presence of an aldehyde, in the presence or absence of a proton source and in the presence or absence of an iron-containing catalyst or a copper-containing catalyst.

DETAILED DESCRIPTION OF THE INVENTION

Examples of the olefin represented by the formula (1) used in the present invention include ethylene, propylene, butene, pentene, hexene, heptene, octene, nonene, decene, undecene, dodecene, pentadecene, eicocene, methylbutene, methylpentene, methylhexene, methylheptene, methyldecene, methyltetradecene, dimethylbutene, dimethylpentene, dimethylhexene, dimethylheptene, dimethyldecene, trimethylnonene, ethylpentene, ethylhexene, ethylheptene, n-propylnonene, tetramethylnonene, tetramethyldecene, ethyl-n-propyldecene, cyclopentene, cyclohexene, cycloheptene, cyclooctene, cyclododecene, methylcyclopentene, methylcyclohexene, ethylcyclohexene, ethylcyclooctene, dimethylcyclohexene, norbornene, pinene, allyl chloride, allyl bromide, crotyl chloride, crotyl bromide, 1,4-dichlorobutene, pentenol, cyclohexenol, terpineol, methyl pentenyl ether, cyclohexenyl ethyl ether, cyclohexenyl phenyl ether, pentenyl acetate, cyclohexenyl acetate, pentenone, hexenone, heptenone, methyl hexenoate, ethyl oleate, phenyl hexenoate, phenyl oleate, styrene, methylstyrene, ethylstyrene, stilbene, p-chlorostyrene, m-chlorostyrene, p-methylstyrene, p-ethylstyrene, p-methoxystyrene, p-ethoxystyrene, methylisoeugenol, m-phenoxystyrene, p-acetoxystyrene, p-acetylstyrene, p-methoxycarbonylstyrene, p-phenoxycarbonylstyrene, phenylbutene, phenylpentene, phenylhexene, phenyloctene, p-chlorophenylbutene, m-chlorophenylbutene, p-methylphenylbutene, p-ethylphenylbutene, p-methoxyphenylbutene, p-ethoxyphenylbutene, m-phenoxyphenylbutene, p-acetoxyphenylbutene, p-acetylphenylbutene, p-methoxycarbonylphenylbutene, p-phenoxycarbonylphenylbutene, cyclohexenone, methyl cinnamate, methyl p-methoxycinnamate, phenyl cinnamate, cholesterol, and cholesteryl acetate. The positions of the substituents in the olefins are optional, and the olefins include, if any, the geometric isomers.

The epoxide which is the intended compound of the present invention can be obtained as the epoxide represented by the formula (2) by using the above-mentioned olefin. Examples of the epoxide include ethylene oxide, propylene oxide, butene oxide, pentene oxide, hexene oxide, heptene oxide, octene oxide, nonene oxide, decene oxide, undecene oxide, dodecene oxide, pentadecene oxide, eicocene oxide, methylbutene oxide, methylpentene oxide, methylhexene oxide, methylheptene oxide, methyldecene oxide, methyltetradecene oxide, dimethylbutene oxide, dimethylpentene oxide, dimethylhexene oxide, dimethylheptene oxide, dimethyldecene oxide, trimethylnonene oxide, ethylpentene oxide, ethylhexene oxide, ethylheptene oxide, n-propylnonene oxide, tetramethylnonene oxide, tetramethyldecene oxide, ethyl-n-propyldecene oxide, cyclopentene oxide, cyclohexene oxide, cycloheptene oxide, cyclooctene oxide, cyclododecene oxide, methylcyclopentene oxide, methylcyclohexene oxide, ethylcyclohexene oxide, ethylcyclooctene oxide, dimethylcyclohexene oxide, norbornene oxide, pinene oxide, epichlorohydrin, epibromohydrin, 1-chloro-2,3-epoxybutane, 1-bromo-2,3-epoxybutane, 1,4-dichloro-2,3-epoxybutane, epoxypentanol, epoxycyclohexanol, terpineol oxide, epoxypentyl methyl ether, epoxycyclohexyl ethyl ether, epoxycyclohexyl phenyl ether, epoxypentyl acetate, epoxycyclohexyl acetate, epoxypentanone, epoxyhexanone, epoxyheptanone, methyl epoxyhexanoate, ethyl epoxyoctadecanoate, phenyl epoxyhexanoate, phenyl epoxyoctadecanoate, styrene oxide, methylstyrene oxide, ethylstyrene oxide, stilbene oxide, p-chlorostyrene oxide, m-chlorostyrene oxide, p-methylstyrene oxide, p-ethylstyrene oxide, p-methoxystyrene oxide, p-ethoxystyrene oxide, 1-(3',4'-dimethoxyphenyl)- 1,2-epoxypropane, p-acetoxystyrene oxide, p-acetylstyrene oxide, p-methoxycarbonylstyrene oxide, p-phenoxycarbonylstyrene oxide, phenylbutene oxide, phenylpentene oxide, phenylhexene oxide, phenyloctene oxide, p-chlorophenylbutene oxide, m-chlorophenylbutene oxide, p-methylphenylbutene oxide, p-ethylphenylbutene oxide, p-methoxyphenylbutene oxide, p-ethoxyphenylbutene oxide, m-phenoxyphenylbutene oxide, p-acetoxyphenylbutene oxide, p-acetylphenylbutene oxide, p-methoxycarbonylphenylbutene oxide, p-phenoxycarbonylphenylbutene oxide, epoxycyclohexanone, methyl 3-phenylglycidate, methyl 3-(4-methoxyphenyl)glycidate, phenyl 3-phenylglycidate, 5,6-epoxy-3-cholestanol and 5,6-epoxy-3-cholestanyl acetate.

Examples of the iron-containing catalyst include Fe, $Fe(CO)_5$, $Fe(CO)_9$, $Fe(CO)_{12}$, FeO, $FeCl_2·nH_2O$, $FeBr_2·nH_2O$, $FeSO_4·nH_2O$, $FeCl_3·nH_2O$, $Fe_2(SO_4)_3·nH_2O$, $Fe(NO_3)_3·nH_2O$, $Fe(OAc)_3$, $Fe_2O_3$ and $Fe_3O_4$, preferably Fe, $FeCl_2·nH_2O$, $FeSO_4·nH_2O$, $FeCl_3·nH_2O$, $Fe(OAc)_3$ and $Fe_2O_3$, more preferably Fe and $Fe_2O_3$. Examples of the copper-containing catalyst include Cu, CuCl, $CuCl_2·nH_2O$, CuBr, $CuBr_2$, CuI, $CuF_2$, $CuSO_4·nH_2O$, $Cu(NO_3)_2·nH_2O$, $Cu(ClO_4)_2·nH_2O$, $Cu(OH)_2$, $Cu(OCH_3)_2$, $Cu_3(PO_4)_2·nH_2O$, $Cu_2O$, CuO and $Cu(OAc)_2·nH_2O$, preferably Cu, CuCl, $Cu(OAc)_2·nH_2O$, $Cu(OH)_2$, $Cu(OCH_3)_2$, $Cu_2O$ and CuO, more preferably Cu, $Cu(OH)_2$, $Cu_2O$ and CuO. In the above examples of the catalysts, n is normally an integer of 0 to 7. These catalysts may also be used as a mixture thereof, or may also be used after supported on heteropolyacids, silica gel, carbon powders, polymers, and other suitable carriers. The amount of the catalyst to be used is not particularly limited but is usually in the range of 0.01%–120% by mole, preferably 0.1%–10% by mole, relative to the olefin.

Examples of the aldehyde include formaldehyde, acetaldehyde, propionaldehyde, butanal, pentanal, hexanal, heptanal, decanal, 2-methylpropanal, 2-methylbutanal, cyclohexanecarboxaldehyde, isovaleraldehyde, benzaldehyde, m-chlorobenzaldehyde, p-chlorobenzaldehyde, p-tolualdehyde, p-anisaldehyde, and pivalaldehyde. When the oxidation is performed in the absence of a catalyst, 2-methylpropanal, 2-methylbutanal, isovaleraldehyde, and pivalaldehyde are preferably used. The amount of the aldehyde to be used is not particularly limited but is usually in the range of 1–30 moles, preferably 1–10 moles, per mole of the olefin.

The addition of a proton source is particularly effective when the transition metal catalyst used is a simple substance. Examples of the proton source include formic acid, acetic acid, monochloroacetic acid, dichloroacetic acid, trichloroacetic acid, monobromoacetic acid, trifluoroacetic acid, propanoic acid, butyric acid, heptanoic acid, decanoic acid, benzoic acid, p-toluenesulfonic acid, hydrochloric acid, hydrogen bromide, sulfuric acid, nitric acid and water, preferably acetic acid and benzoic acid. The amount of the proton source to be used is not particularly limited, but is usually in the range of 1–100 moles per mole of the iron-containing or copper-containing catalyst. When the iron-containing or copper-containing catalyst contains water, however, the use of the proton source is not necessary.

In the process of the present invention, the reaction may also be performed in a solvent. Examples of the solvent which may be used include halogenated hydrocarbons such as dichloromethane, chloroform and ethylene dichloride, esters such as ethyl acetate, nitriles such as acetonitrile and aromatic hydrocarbons such as benzene, toluene, xylene, monochlorobenzene and dichlorobenzene.

The oxygen used in the present invention may be, besides oxygen, also air. The method of supplying the oxygen is not particularly restricted, and the reaction is generally conducted by blowing oxygen into the system, or under oxygen atmosphere, or supplying oxygen by other suitable means.

The method of feeding the olefin is not particularly limited but, when $Fe_2O_3$ is used, the olefin is preferably fed last.

The reaction temperature is usually in the range from 0° C. to the reflux temperature of the reaction mixture, preferably in the range from 20° C. to 80° C.

The reaction time is not particularly limited. The reaction mixture may be analyzed by means of GC (gas chromatography) or the like, and the time at which the conversion to the intended epoxide levels off may be taken as the end point of the reaction. The reaction times is usually in the range from 1 to 48 hours.

In the present reaction, the aldehyde used is converted into the corresponding carboxylic acid and can be easily separated from the intended product.

After completion of the reaction, the intended epoxide can be obtained, for example, by recovering the catalyst by filtration and then subjecting the filtrate to washing with aqueous sodium hydrogencarbonate solution, then concentration and, if necessary, further operations such as rectification.

The process of the present invention is an industrially excellent one which can produce a corresponding epoxide from an olefin through a reaction with oxygen in the presence of an aldehyde, in the presence or absence of a proton source, and in the absence of a catalyst or by using an iron-containing or copper-containing catalyst which is easily available and recoverable and which brings little of undesirable substances into the waste water.

The present invention will be described in more detail below with reference to Examples, but it is in no way limited thereto.

EXAMPLE 1

A mixture of 164 mg of cyclohexene, 433 mg of 2-methylpropanal and 10 ml of dichloromethane was stirred overnight under an oxygen atmosphere at 25° C. Analysis of the reaction mixture by GC showed that cyclohexene oxide had been formed in 90% yield.

EXAMPLE 2

A mixture of 272 mg of α-pinene, 517 mg of isovaleraldehyde and 10 ml of dichloromethane was stirred overnight under an oxygen atmosphere at 25° C. Analysis of the reaction mixture by GC showed that α-pinene oxide had been formed in 86% yield.

EXAMPLE 3

A mixture of 164 mg of cyclohexene, 517 mg of 2-metylbutanal and 10 ml of dichloromethane was stirred overnight under an oxygen atmosphere at 25° C. Analysis of the reaction mixture by GC showed that cyclohexene oxide had been formed in 88% yield.

EXAMPLES 4–6

Mixtures of 2 mmoles of an olefin, 517 mg of pivalaldehyde and 10 ml of dichloromethane were stirred overnight under an oxygen atmosphere at 25° C. Analysis of the reaction mixtures by GC gave the results shown in Table 1.

TABLE 1

| Example No. | Olefin | Product | Yield[1] (%) |
|---|---|---|---|
| 4 | 1-Decene | 1-Decene oxide | 65 |
| 5 | trans-5-Decene | trans-5-Decene oxide | 92 |
| 6 | cis-Stilbene | cis-Stilbene oxide | 38 |
|  |  | trans-Stilbene oxide | 48 |

Note:
[1] Based on olefin

EXAMPLES 7–12

A solution of 914 mg of heptanal in 2 ml of dichloromethane was added dropwise over a period of 1 hour to respective mixtures of 164 mg of cyclohexene, 1% by mole (relative to cyclohexene) of a catalyst, 1.2 mg of acetic acid and 10 ml of dichloromethane under an oxygen atmosphere at 25° C., and the resulting mixtures were stirred for further 15 hours at the same temperature. Analysis of the reaction mixtures by GC gave the results shown in Table 2.

TABLE 2

| Example No. | Catalyst | Cyclohexene oxide yield[1] (%) |
|---|---|---|
| 7 | Fe | 71 |
| 8 | $FeCl_2.4H_2O$ | 6 |
| 9 | $FeSO_4.7H_2O$ | 18 |
| 10 | $FeCl_3.6H_2O$ | 8 |
| 11 | $Fe(OAc)_3$ | 30 |
| 12 | $Fe_2O_3$ | 10 |

Note:
[1] Based on cyclohexene

EXAMPLES 13 18

Mixtures of 281 mg of 1-decene, 1% by mole (relative to 1-decene) of a catalyst, 1.2 mg of acetic acid, 685 mg of heptanal and 10 ml of dichloromethane were stirred under an oxygen atmosphere at 25° C. for 17 hours. Analysis of the reaction mixtures gave the results shown in Table 3.

TABLE 3

| Example No. | Catalyst | Conversion[1] | 1-Decene oxide yield[2] (%) |
|---|---|---|---|
| 13 | Fe | 56 | 52(92) |
| 14 | $FeCl_2.4H_2O$ | 11 | 5(49) |
| 15 | $FeSO_4.7H_2O$ | 5 | 4(81) |
| 16 | FeO | 6 | 5(84) |
| 17 | $FeCl_3.6H_2O$ | 6 | 4(65) |
| 18 | $Fe(OAc)_3$ | 9 | 7(82) |

Note:
[1] Based on 1-decene.
[2] Based on 1-decene. Values in parenthesis are based on converted 1-decene.

EXAMPLES 19–24

Mixtures of 281 mg of 1-decene, 1.1 mg of Fe, 1.2 mg of acetic acid, 6 mmoles of an aldehyde and 10 ml of dichloromethane were stirred under an oxygen atmosphere at 25° C. for 17 hours. The reaction mixtures were analyzed by GC to obtain the results shown in Table 4.

TABLE 4

| Example No. | Aldehyde | Conversion[1] (%) | 1-Decene oxide yield[2] (%) |
|---|---|---|---|
| 19 | Acetaldehyde | 3 | 3(100) |
| 20 | Butanal | 73 | 59 (81) |
| 21 | 2-Methylpropanal | 37 | 28 (75) |
| 22 | Cyclohexane-carboxaldehyde | 30 | 25 (84) |
| 23 | Pivalaldehyde | 44 | 32 (73) |
| 24 | Benzaldehyde | 16 | 12 (77) |

Note:
[1] Based on 1-decene.
[2] Based on 1-decene. Values in parenthesis are based on converted 1-decene.

EXAMPLES 25–29

Mixtures of 281 mg of 1-decene, 1.1 mg of Fe, 1% by mole (relative to 1-decene) of an acid, 685 mg of heptanal and 10 ml of dichloromethane were stirred under an oxygen atmosphere at 25° C. for 17 hours. The reaction mixtures were analyzed by GC to obtain the results shown in Table 5.

TABLE 5

| Example No. | Acid | Conversion[1] (%) | 1-Decene oxide yield[2] (%) |
|---|---|---|---|
| 25 | Benzoic acid | 59 | 56(95) |
| 26 | Formic acid | 56 | 51(91) |
| 27 | Heptanoic acid | 58 | 53(91) |
| 28 | Trifluoroacetic acid | 58 | 45(78) |
| 29 | p-toluene-sulfonic acid | 41 | 39(94) |

Note:
[1] Based on 1-decene.
[2] Based on 1-decene. Values in parenthesis are based on converted 1-decene.

EXAMPLES 30–32

Mixtures of 281 mg of 1-decene, 1.1 mg of Fe, 2.4 mg of benzoic acid, 685 mg of heptanal and 10 ml of a solvent were stirred under an oxygen atmosphere at 25° C. for 17 hours. The reaction mixtures were analyzed by GC to obtain the results shown in Table 6.

TABLE 6

| Example No. | Solvent | conversion*[1] (%) | 1-Decene oxide yield*[2] (%) |
|---|---|---|---|
| 30 | Acetonitrile | 61 | 56(92) |
| 31 | Benzene | 31 | 31(99) |
| 32 | Ethyl acetate | 12 | 12(99) |

Note:
*[1] Based on 1-decene.
*[2] Based on 1-decene. Values in parenthesis are based on converted 1-decene.

EXAMPLES 33–34

Mixtures of 281 mg of 1-decene, 1.1 mg of Fe, 2.4 mg of benzoic acid, heptanal and 10 ml of dichloromethane were stirred under an oxygen atmosphere at 25° C. for 17 hours. The reaction mixtures were analyzed by GC to obtain the results shown in Table 7.

TABLE 7

| Example No. | Heptanal equivalent (relative to 1-decene) | Conversion*[1] (%) | 1-Decene oxide yield*[2] (%) |
|---|---|---|---|
| 33 | 2 | 38 | 37(98) |
| 34 | 4 | 64 | 55(86) |

Note:
*[1] Based on 1-decene.
*[2] Based on 1-decene. Values in parenthesis are based on converted 1-decene.

EXAMPLES 35–37

Mixtures of 281 mg of 1-decene, Fe, 2.4 mg of benzoic acid, 685 mg of heptanal and 10 ml of dichloromethane were stirred under an oxygen atmosphere at 25° C. for 17 hours. The reaction mixtures were analyzed by GC to obtain the results shown in Table 8.

TABLE 8

| Example No. | Fe equivalent (relative to 1-decene) | Conversion*[1] (%) | 1-Decene oxide yield*[2] (%) |
|---|---|---|---|
| 35 | 0.001 | 58 | 52(89) |
| 36 | 0.05 | 56 | 48(85) |
| 37 | 0.10 | 56 | 47(83) |

Note:
*[1] Based on 1-decene.
*[2] Based on 1-decene. Values in parenthesis are based on converted 1-decene.

EXAMPLES 38–45

Mixtures of 2 mmoles of an olefin, 1.1 mg of Fe, 2.4 mg of benzoic acid, 685 mg of heptanal and 10 ml of dichloromethane were stirred under an oxygen atmosphere at 25° C. for 17 hours. The reaction mixtures were analyzed by GC to obtain the results shown in Table 9.

TABLE 9

| Example No. | Olefin | Conversion*[1] (%) | Product | Yield*[2] (%) |
|---|---|---|---|---|
| 38 | Cyclohexene | 100 | Cyclohexene oxide | 79 (79) |
| 39 | trans-5-Decene | 100 | trans-5-Decene oxide | 89 (89) |
| 40 | cis-5-Decene | 100 | cis-5-Decene oxide | 56 (56) |
|  |  |  | trans-5-Decene oxide | 30 (30) |
| 41 | 1-Methyl-cyclohexene | 29 | 1-Methylcyclohexene oxide | 29(100) |
| 42 | α-Pinene | 23 | α-Pinene oxide | 23 (99) |
| 43 | trans-Stilbene | 14 | trans-Stilbene oxide | 12 (84) |
| 44 | cis-Stilbene | 28 | cis-Stilbene oxide | 5 (16) |
|  |  |  | trans-Stilbene oxide | 21 (76) |
| 45 | 2-Cyclohexenol | 100 | 2,3-Epoxy-1-cyclohexanol | 38 (38) |

Note:
*[1] Based on olefin
*[2] Based on olefin. Values in parenthesis are based on converted olefin.

EXAMPLES 46–50

Examples 38–45 were repeated except that 517 mg of pivalaldehyde was used in place of 685 mg of heptanal, to obtain the results shown in Table 10.

TABLE 10

| Example No. | Olefin | Conversion*[1] (%) | Product | Yield*[2] (%) |
|---|---|---|---|---|
| 46 | 1-Methyl-cyclohexene | 100 | 1-Methyl-cyclohexene oxide | 88(88) |
| 47 | α-Pinene | 100 | α-Pinene oxide | 81(81) |
| 48 | trans-Stilbene | 100 | trans-Stilbene oxide | 90(90) |
| 49 | cis-Stilbene | 66 | cis-Stilbene oxide | 9(13) |
|  |  |  | trans-Stilbene oxide | 44(66) |
| 50 | Methyl p-methoxy-cinnamate | 47 | Methyl 3-(4-methoxy-phenyl)glycidate | 43(90) |

Note:
*[1] Based on olefin.
*[2] Based on olefin. Values in parenthesis are based on converted olefin.

EXAMPLES 51–54

Mixtures of 272 mg of α-pinene, 1.1 mg of Fe, 2.4 mg of benzoic acid, 6 mmoles of an aldehyde and 10 ml of dichloromethane were stirred under an oxygen atmosphere at 25° C. for 17 hours. The reaction mixtures were analyzed by GC to obtain the results shown in Table 11.

TABLE 11

| Example No. | Aldehyde | Conversion*[1] (%) | α-Pinene oxide Yield*[2] (%) |
|---|---|---|---|
| 51 | Butanal | 11 | 11(98) |
| 52 | Isovaleraldehyde | 42 | 33(79) |
| 53 | 2-Methylpropanal | 91 | 72(79) |
| 54 | Benzaldehyde | 12 | 11(98) |

TABLE 11-continued

| Example No. | Aldehyde | Conversion*[1] (%) | α-Pinene oxide Yield*[2] (%) |
|---|---|---|---|

Note:
*[1]Based on α-pinene.
*[2]Based on α-pinene. Values in parenthesis are based on converted α-pinene.

EXAMPLE 55

A solution of 1.83 g of heptanal in 4 ml of dichloromethane was added dropwise over a period of 1 hour to a mixture of 561 mg of trans-5-decene, 2.2 mg of Fe, 2.4 mg of acetic acid and 20 ml of dichloromethane under an oxygen atmosphere at 25° C., and the resulting mixture was stirred for further 15 hours at the same temperature. The reaction mixture was analyzed by GC to obtain the following results.

Conversion: 87% trans-5-Decene oxide yield:

84% (based on trans-5-decene)

97% (based on converted trans-5-decene)

cis-5-Decene oxide yield:

3% (based on trans-5-decene)

3% (based on converted trans-5-decene)

EXAMPLES 56–66

A mixture of 637 mg of benzaldehyde, 3.2 mg of $Fe_2O_3$ and 12 ml of benzene was stirred vigorously under an oxygen atmosphere at room temperature, and then 2 mmoles of an olefin was added thereto over a period of 0.5 hours. After completion of the addition, the mixture was stirred for further 17 hours at the same temperature. The reaction mixture was analyzed by GC to obtain the results shown in Table 12.

TABLE 12

| Example No. | Olefin | Conversion*[1] (%) | Product | Yield*[2] (%) |
|---|---|---|---|---|
| 56 | Cyclohexene | 100 | Cyclohexene oxide | 97 (97) |
| 57 | α-Pinene | 100 | α-Pinene oxide | 90 (90) |
| 58 | Styrene | 100 | Styrene oxide | 85 (85) |
| 59 | p-Chlorostyrene | 100 | p-Chlorostyrene oxide | 81 (81) |
| 60 | p-Methoxystyrene | 100 | p-Methoxystyrene oxide | 89 (89) |
| 61 | Crotyl bromide | 96 | 1-Bromo-2,3-epoxybutane | 96(100) |
| 62 | trans-1,4-Dichloro-2-butene | 91 | trans-1,4-Dichloro-2,3-epoxybutane | 90 (99) |
| 63 | Norbornene | 100 | Norbornene oxide | 100(100) |
| 64 | α-Terpineol | 100 | α-Terpineol oxide | 80 (80) |
| 65 | Methylisoeugenol | 98 | 1-(3,4-Dimethoxyphenyl)-1,2-epoxy-propane | 84 (86) |
| 66 | Cholesteryl acetate | — | 5,6-Epoxy-3-cholestanyl acetate | 88*[3] |

Note:
*[1]Based on olefin.

TABLE 12-continued

| Example No. | Olefin | Conversion*[1] (%) | Product | Yield*[2] (%) |
|---|---|---|---|---|

*[2]Based on olefin. Values is parenthesis are based on converted olefin.
*[3]Isolated yield

EXAMPLES 67–71

A solution of 897 mg of cyclohexanecarboxaldehyde in 2 ml of dichloromethane was added dropwise over a period of 2 hours to a mixture of 164 mg of cyclohexene, 3% by mole (relative to cyclohexene) of a catalyst, 1.2 mg of acetic acid and 10 ml of dichloromethane under an oxygen atmosphere at 25° C., and the resulting mixture was stirred at the same temperature for further 15 hours. The reaction mixture was analyzed by GC to obtain the results shown in Table 13.

TABLE 13

| Example No. | Catalyst | Cyclohexene oxide yield*[1] (%) |
|---|---|---|
| 67 | Cu | 80 |
| 68 | $Cu(OAc)_2$ | 85 |
| 69 | CuCl | 78 |
| 70 | $Cu_2O$ | 82 |
| 71 | CuO | 75 |

Note:
*[1]Based on cyclohexene.

EXAMPLES 72–75

Mixtures of 281 mg of 1-decene, 1% by mole (relative to 1-decene) of a catalyst, 637 mg of benzaldehyde and 12 ml of dichloromethane were stirred under an oxygen atmosphere at 25° C. for 17 hours. The reaction mixtures were analyzed by GC to obtain the results shown in Table 14.

TABLE 14

| Example No. | Catalyst | Conversion*[1] (%) | 1-Decene oxide yield*[2] (%) |
|---|---|---|---|
| 72 | $Cu(OCH_3)_2$ | 53 | 30(57) |
| 73 | $Cu(OH)_2$ | 51 | 32(64) |
| 74 | Cu | 42 | 26(60) |
| 75 | $Cu(OAc)_2$ | 40 | 25(63) |

Note:
*[1]Based on 1-decene.
*[2]Based on 1-decene. Values in parenthesis are based on converted 1-decene.

EXAMPLES 76–82

Mixtures of 2 mmoles of an olefin, 1.0 mg of $Cu(OH)_2$, 673 mg of cyclohexanecarboxaldehyde and 12 ml of dichloromethane were stirred under an oxygen atmosphere for 17 hours. The reaction mixtures were analyzed by GC to obtain the results shown in Table 15.

TABLE 15

| Example No. | Olefin | Conversion*[1] (%) | Product | Yield*[2] (%) |
|---|---|---|---|---|
| 76 | 1-Decene | 51 | 1-Decene oxide | 27(83) |
| 77 | Cyclohexene | 100 | Cyclohexene oxide | 79(79) |

TABLE 15-continued

| Example No. | Olefin | Conversion*[1] (%) | Product | Yield*[2] (%) |
|---|---|---|---|---|
| 78 | trans-5-Decene | 83 | trans-5-Decene oxide | 80(96) |
| 79 | cis-5-Decene | 96 | cis-5-Decene oxide | 19(20) |
| | | | trans-5-Decene oxide | 63(66) |
| 80 | α-Pinene | 100 | α-Pinene oxide | 84(84) |
| 81 | trans-Stilbene | 93 | trans-Stilbene oxide | 76(82) |
| 82 | cis-Stilbene | 81 | cis-Stilbene oxide | 7 (9) |
| | | | trans-Stilbene oxide | 57(70) |

Note:
*[1]Based on olefin.
*[2]Based on olefin. Values in parenthesis are based on converted olefin.

What is claimed is:

1. A process for producing an epoxide represented by the formula (2)

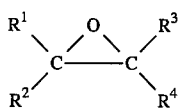

wherein $R^1$, $R^2$, $R^3$ and $R^4$ may be the same or different and each denotes a hydrogen atom, ($C_1$–$C_{20}$) alkyl group, alkyl group substituted with a halogen, hydroxy, alkoxy, phenoxy, acyloxy, acyl, alkoxycarbonyl or phenoxycarbonyl; phenyl group, phenyl group substituted with a halogen, alkyl, alkoxy, phenoxy, acyloxy, acyl, alkoxycarbonyl or phenoxycarbonyl; phenylalkyl group, phenylalkyl group substituted with a halogen, alkyl, alkoxy, phenoxy, acyloxy, acyl, alkoxycarbonyl, or phenoxycarbonyl; acyl group, alkoxycarbonyl group or phenoxycarbonyl group; provided that $R^1$ and $R^2$ or $R^3$ and $R^3$ may combine with each other to form a ring, or $R^1$, $R^2$ and $R^3$ may combine altogether to form a condensed ring, which comprises reacting an olefin represented by the formula (1)

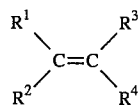

wherein $R^1$, $R^2$, $R^3$ and $R^4$ are the same as defined above, with oxygen in the presence of a ($C_3$–$C_7$) aldehyde and a catalyst which is CuO, is a member selected from the group consisting of Cu, Cu(OH)$_2$, and Cu$_2$O, or is a CuO-free mixture of copper-containing compounds containing at least one member selected from the group consisting of Cu, Cu(OH)$_2$, and Cu$_2$O.

2. A process for producing an epoxide represented by the formula (2)

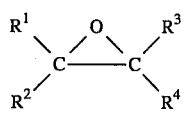

wherein $R^1$, $R^2$, $R^3$ and $R^4$ may be the same or different and each denotes a hydrogen atom, ($C_1$–$C_{20}$) alkyl group, alkyl group substituted with a halogen, hydroxy, alkoxy, phenoxy, acyloxy, acyl, alkoxycarbonyl or phenoxycarbonyl; phenyl group, phenyl group substituted with a halogen, alkyl, alkoxy, phenoxy, acyloxy, acyl, alkoxycarbonyl or phenoxycarbonyl; phenylalkyl group, phenylalkyl group substituted with a halogen, alkyl, alkoxy, phenoxy, acyloxy, acyl, alkoxycarbonyl, or phenoxycarbonyl; acyl group, alkoxycarbonyl group or phenoxycarbonyl group; provided that $R^1$ and $R^2$ or $R^3$ and $R^3$ may combine with each other to form a ring, or $R^1$, $R^2$ and $R^3$ may combine altogether to form a condensed ring, which process comprises the step of reacting an olefin represented by the formula ( 1 )

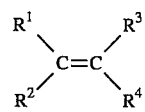

wherein $R^1$, $R^2$, $R^3$ and $R^4$ are the same as defined above, with oxygen in the presence of a ($C_3$–$C_7$) aldehyde and a catalyst which consists of at least one member selected from the group consisting of Cu, Cu(OH)$_2$, Cu$_2$O, CuO, CuCl, CuCl$_2$·nH$_2$O, CuBr, CuBr$_2$, CuI, CuF$_2$, CuSO$_4$·nH$_2$O, Cu(NO$^3$)$_2$ ·nH$_2$O, Cu(ClO$_4$)$_2$·nH$_2$O, Cu (OCH$_3$)$_2$, Cu$_3$ ( PO$_4$)$_2$·nH$_2$O, and Cu(OAc)$_2$·nH$_2$O.

3. A process for producing an epoxide according to claim 1 or 2, wherein the reaction is conducted in the presence of a proton source.

4. The process according to claim 1 or 2, wherein the reaction is conducted in the presence of a proton source which is acetic acid or benzoic acid.

5. The process according to claim 1 or 2, wherein the reaction is conducted in the presence of 1–100 moles of a proton source per mole of the catalyst.

6. The process according to claim 1 or 2, wherein the amount of the aldehyde is 1–30 moles per mole of the olefin.

7. The process according to claim 1 or 2, wherein the amount of the catalyst is 0.01%–120% by mole relative to the olefin.

8. The process according to claim 1 or 2, wherein the reaction is performed in a solvent.

9. The process according to claim 1 or 2, wherein the reaction is performed in a solvent which is dichloromethane, ethyl acetate, acetonitrile or benzene.

10. The process according to claim 1 or 2, wherein the reaction temperature is 0° C. to the reflux temperature of the reaction mixture.

11. The process according to claim 1 or 2, wherein the reaction time is 1 to 48 hours.

12. The process according to claim 1 or 2, wherein the oxygen is supplied by blowing it into the reaction system.

* * * * *